US00PP15053P2

(12) United States Plant Patent
Olesen et al.

(10) Patent No.: US PP15,053 P2
(45) Date of Patent: Jul. 27, 2004

(54) FLORIBUNDA ROSE PLANT NAMED 'POULFL002'

(50) Latin Name: *Rosa hybrida*
Varietal Denomination: POULfl002

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 10/685,543

(22) Filed: Oct. 14, 2003

(51) Int. Cl.[7] ..... A01H 5/00
(52) U.S. Cl. ..... Plt./149
(58) Field of Search ..... Plt./149, 148, 107, Plt./137, 138

*Primary Examiner*—Anne Marie Grunberg
*Assistant Examiner*—June Hwu

(57) ABSTRACT

A new floribunda garden rose plant which has abundant, pink and orange blend flowers and attractive foliage. This new and distinct variety has shown to be uniform and stable in the resulting generations from asexual propagation.

2 Drawing Sheets

Botanical classification: *Rosa hybrida.*
Variety denomination: 'POULfl002'.

The present invention constitutes a new and distinct variety of garden rose plant which originated from a controlled crossing between a female parent 'POULskov', described and illustrated in U.S. Plant Pat. No. 9,062 issued on Feb. 28, 1995 and the male parent, an un-named, non-patented rose plant. The two parents were crossed during the summer of 1991 and the resulting seeds were planted in a controlled environment in Fredensborg, Denmark. The new variety is named 'POULfl002'.

The new variety may be distinguished from its pollen parent, an un-named plant, by the following combination of characteristics:

1. The pollen parent has an average flower diameter of 60 mm when open, while that of 'POULfl002' is 65 mm.
2. After opening, the upper surface of the flower petals of the pollen parent are Red Purple Group 70C and 70D while the same on 'POULfl002' is Red Group 55D.

The new variety may be distinguished from its seed parent, 'POULskov' by the following combination of characteristics:

1. 'POULskov' has an average bloom diameter, when opened, of 60 to 80 mm, while 'POULfl002' is 65 mm.
2. General tonality of 'POULskov' is Red Group 49D to 56D, while 'POULfl002' is Red 52D.

The objective of the hybridization of this rose variety was to create a new and distinct variety for garden use with unique qualities, such as:

1. Uniform and abundant pink orange blend flowers;
2. Vigorous, but compact growth when propagated both as a budded rose and on its own roots;
3. Disease resistance;
4. Continuous flowering;
5. Dark green glossy foliage.

This combination of qualities is not present in previously available commercial cultivars of this type, known to the inventors, and distinguish 'POULfl002' from all other varieties of which we are aware.

As part of their rose development program, L. Pernille Olesen and Mogens N. Olesen germinated the seeds from the aforementioned hybridization during winter 1991 and conducted evaluations on the resulting seedlings in a controlled environment in Fredensborg, Denmark.

'POULfl002' was selected in the spring 1992 by the inventors as a single plant from the progeny of the aforementioned hybridization.

Asexual reproduction of 'POULfl002' by traditional budding and rooted cuttings was first done by L. Pernille and Mogens N. Olesen in their nursery in Fredensborg, Denmark in July, 1992. This initial and other subsequent asexual propagations conducted in controlled environments have demonstrated that the characteristics of 'POULfl002' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'POULfl002'. Specifically illustrated in FIG. 1:

FIG. 1.1; Open flower viewed from above, and open flower side view showing attachment of sepals and peduncle;

FIG. 1.2; Flower bud, closed, sepals unfolding, partially open, and open with sepals fully retracted;

FIG. 1.3; Flower petals, detached; Specifically illustrated in FIG. 2:

FIG. 2.1; Sepals, receptacle, and peduncle;

FIG. 2.2; Juvenile and mature stem exhibiting thorns;

FIG. 2.3; Leaves.

DETAILED DESCRIPTION OF THE VARIETY

The following is a description of 'POULfl002', as observed in its growth in a field nursery in Jackson County, Oreg. Observed plants are 4 years of age, budded on *Rosa multiflora* understock. Color references are made using The Royal Horticultural Society (London, England) Colour Chart, 1995, except where common terms of color are used.

For a comparison, several physical characteristics of the rose variety 'POULskov', a rose variety from the same inventors described and illustrated in U.S. Plant Pat. No. 9,062 and issued on Feb. 25, 1995 are compared to 'POULfl002' in Chart 1.

CHART 1

| | 'POULf1002' | 'POULskov' |
|---|---|---|
| General tonality of open flower | Red Group 52D | Red Group 49D to 56D |
| Peduncle length | 40 to 50 mm. | 35 to 45 mm. |
| Petal Count | 20 to 25. | 48 to 62. |

Parents:

*Seed parent.*—'POULskov'.

*Pollen parent.*—Unnamed plant.

FLOWER AND FLOWER BUD

Blooming habit: Continuous.

Flower bud:

*Size.*—Upon opening, 23 mm in length from base of receptacle to end of bud. Bud diameter is 16 mm.

*Bud form.*—Pointed ovoid slightly broad based.

*Bud color.*—As sepals unfold, petals are Red-Purple Group 58A to Red Group 52A.

*Sepals.*—Color: Upper Surface is Yellow-Green Group 146 B to Yellow-Green Group 144B. Anthocyanin of Grey-Orange Group 176A observed covering up to one half of the upper surface of the sepal. Lower surface is Yellow-Green Group 144A to 144B. Anthocyanin the color of Greyed-Red Group 181A observed. Surface Texture: Upper surface of sepals is slightly pubescent. Lower surface is sometimes smooth, otherwise covered with prickles. Margins: Stipitate glands observed on all sepal margins. Margins are entire on 2 of the 5 sepals. Medium foliaceous appendages and serrations occur on 3 of the 5 sepals. Shape: Overall sepal shape is subulate. Sepal apex is cirrhose. Base is flat at union with receptacle. Size: 35 mm long×8 mm wide.

*Receptacle.*—Surface: Smooth and glaucous. Few stipitate glands observed. Shape: Urn-shaped. Size: 6 mm (h)×8 mm (w). Color: Yellow-Green Group 144A.

*Peduncle.*—Surface: Dense Rough prickles observed. Length: 40 to 50 mm average length. Color: Yellow-Green Group 144B. Anthocyanin: Greyed-Orange Group 176A to Greyed-Purple Group 183C observed. Strength: Strong, erect.

*Borne.*—Sometimes borne singularly, however in most cases flower buds appear in clusters of 5 buds per flowering stem.

Flower bloom:

*Fragrance.*—Light floral scent with apple overtones.

*Duration.*—The blooms have a duration on the plant of approximately 7 to 10 days. Afterwards, petals usually fall cleanly away from plant.

*Size.*—Average flower diameter is 65 mm when open. Average flower depth is 35 mm.

*Form.*—Generally, the flowers of 'POULfl002' resemble a reflexed open cup.

*Shape of flower when viewed from the side.*—Upon opening, upper part: Flat. Upon opening, lower part: Flat. Open flower, upper part: Convex. Open flower, lower part: Concave.

*Petalage.*—Semi double. Average range: 20 to 25 petals under normal conditions with 5 petaloids.

Color:

*Upon opening, petals.*—Outermost petals: Outer side: Red Group 52D with intonations of Red Group 53D and Red-Purple Group 58A. Inner Side: Red Group 43D with light intonations of Red Group 43C. Innermost petals: Outer side: Red Group 38A. Inner Side: Red Group 41C.

*Upon opening, basal petal spots.*—Outermost petals: Outer side: Yellow Group 12C. Inner Side: Yellow Group 12A. Innermost petals: Outer side: Yellow Group 12A. Inner Side: Yellow Group 12A.

*After opening, petals.*—Outermost petals: Outer side: Red Group 49A to Red Group 48C. Inner Side: Red Group 48D. Innermost petals: Outer side: Red Group 49A to Red Group 48C. Inner Side: Red Group 48D.

*After opening, basal petal spots.*—Outermost petals: Outer Side: Yellow Group 12D. Inner Side: Yellow Group 12B. Innermost petals: Outer Side: Yellow Group 12B. Inner Side: Yellow Group 12B.

General tonality: On an open flower Red Group 49A to 52D. At the end of the 10th day tonality fades to Red Group 49A to 49B.

Petals:

*Petal reflex.*—Somewhat reflexed to strongly.

*Petal edge.*—Entire with weak undulations of the petal margin.

*Shape.*—Apex: Round. Base: Acute.

*Size.*—40 mm long by 35 mm wide.

*Thickness.*—Above average.

*Texture.*—Smooth.

*Arrangement.*—Formal.

Petaloids:

*Quantity.*—3 to 5.

*Shape.*—Elliptical and irregular or asymmetrical.

*Size.*—22 mm (L)×8 mm (W).

*Color.*—Red Group 48D. Basal petal spot is Yellow Group 12B and Yellow Group 11D distinctly.

Reproductive organs:

*Pistils.*—Length: 7 to 8 mm long. Quantity: 64.

*Pollen.*—None-Observed.

*Anthers.*—Size: 2 mm long. Color: Yellow Orange Group 23A. Quantity: 82.

*Filaments.*—Color: Yellow Orange Group 21B. Length: 7 to 8 mm.

*Stigmas.*—Level with anthers in terms of length. Color: Greyed-Yellow Group 160C.

*Styles.*—Color: Greyed-Yellow Group 160C.

*Hips.*—None Observed in the field nursery in Jackson County Oreg.

PLANT

Plant growth: Upright to bushy. When grown as a budded field grown plant on *Rosa multiflora* understock, the average height of the plant is 150 cm and the average width is 100 cm.

Stems:

*Color.*—Young wood: Yellow-Green Group 144B. Mature wood: Yellow-Green Group 144A.

*Internode distance.*—30 to 40 cm.

*Surface texture.*—Young wood: Smooth. Older wood: Rough.

*Thorns.*—Incidence: 4 to 6 thorns per 10 cm of stem. Size: Average length: 10 mm. Color: Greyed-Orange Group 165A. Shape: Linear to concave.

Plant foliage: Normal number of leaflets on normal leaves in middle of the stem: 5 leaflets.

*Compound leaf size.*—100 to 200 mm (l)×80 to 150 mm (w).

*Quantity.*—2 to 3 leaves per 10 cm of stem.

*Color.*—Mature Foliage: Upper Leaf Surface: Green Group 137A to Green 139A. Lower Leaf Surface: Yellow-Green Group 148B to Green Group 138B. Juvenile foliage: Upper Leaf Surface: Green Group 137A to Green 139A. Lower Leaf Surface: Yellow-Green Group 148B to Green Group 138B. Anthocyanin intonation: Not observed.

Plant leaves and leaflets:

*Stipules.*—Size: 15 mm in length by 8 mm wide. Color: Yellow-Green Group 146B. Margin: Stipitate glands observed in medium quantity. Shape: Narrow at the base, widening towards the mid an upper portion. Apecies Extend upward and out.

*Petiole.*—Length: 30 to 35 mm. Diameter: 1.5 to 2 mm. Color: Upper surface is Yellow-Green Group 146B. Lower surface is Yellow-Green Group 144B. Underneath: Thorns observed. Above: Stipitate glands observed.

*Rachis.*—Length: 40 to 45 mm. Color: Upper surface is Yellow-Green Group 146B. Lower surface is Yellow-Green Group 144B. Underneath: Thorns observed. Above: Stipitate glands observed.

*Leaflet.*—Edge: Serrated. Size of Terminal Leaflet: 47 to 95 mm in length by 37 to 75 mm in width. Shape: Generally Ovate sometimes round. Apex is cuspidate. Base shape is round. Texture: Smooth. Arrangement: Odd pinnate. Venation: Reticulate. Glossiness: Moderately glossy.

Disease resistance: Above average resistance to mildew, rust, black spot, and Botrytis under normal growing conditions in Jackson County, Oreg.

Cold hardiness: The variety 'POULfl002' has been found to be cold tolerant to USDA Cold Hardiness Zone 6.

We claim:

1. A new and distinct variety of rose plant of the floribunda rose class, substantially as herein illustrated and described as a distinct and novel rose variety due to its abundant pink and orange blend flowers, disease resistance, and extended period of bloom.

* * * * *

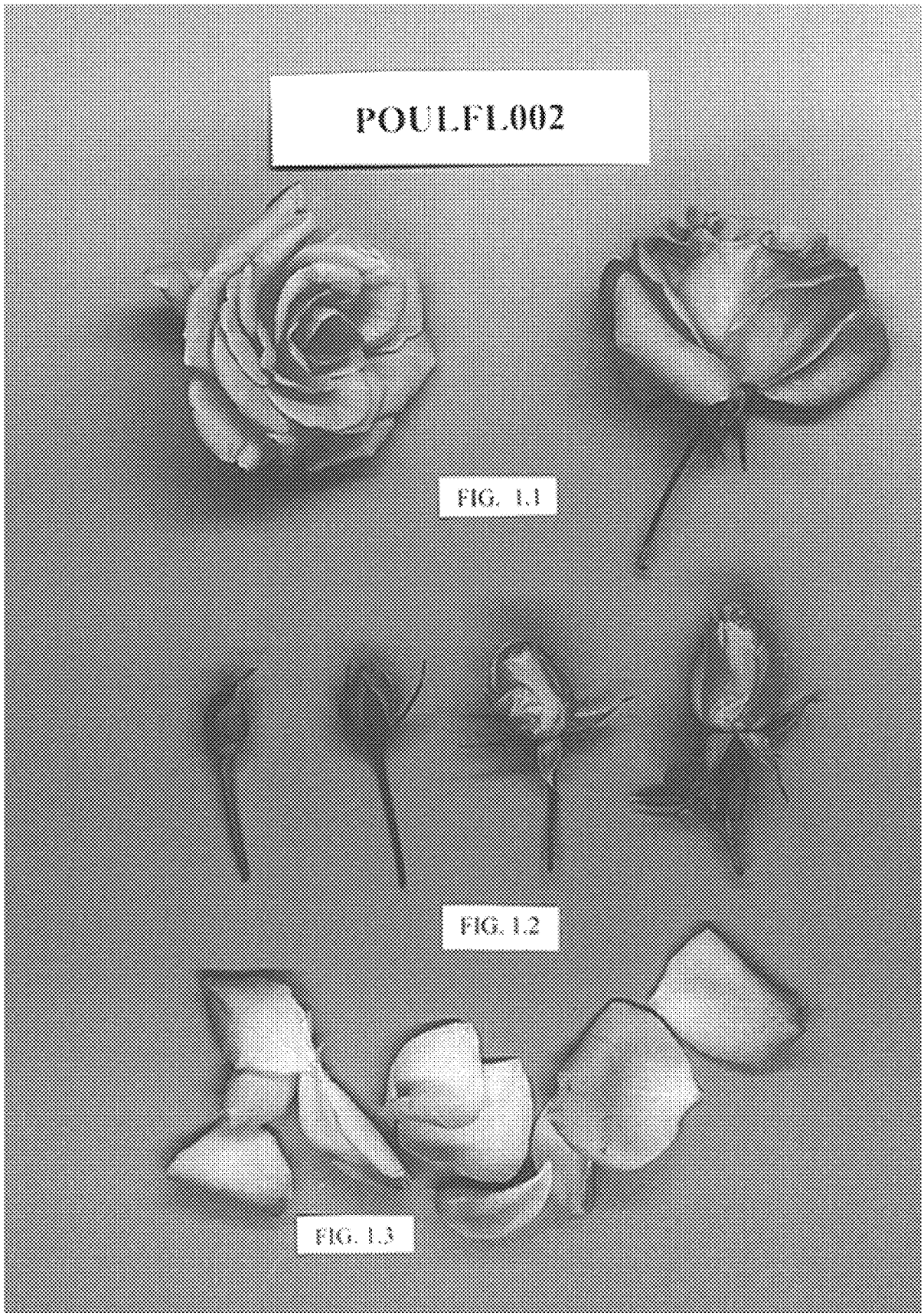
POULFL002
FIG. 1.1
FIG. 1.2
FIG. 1.3

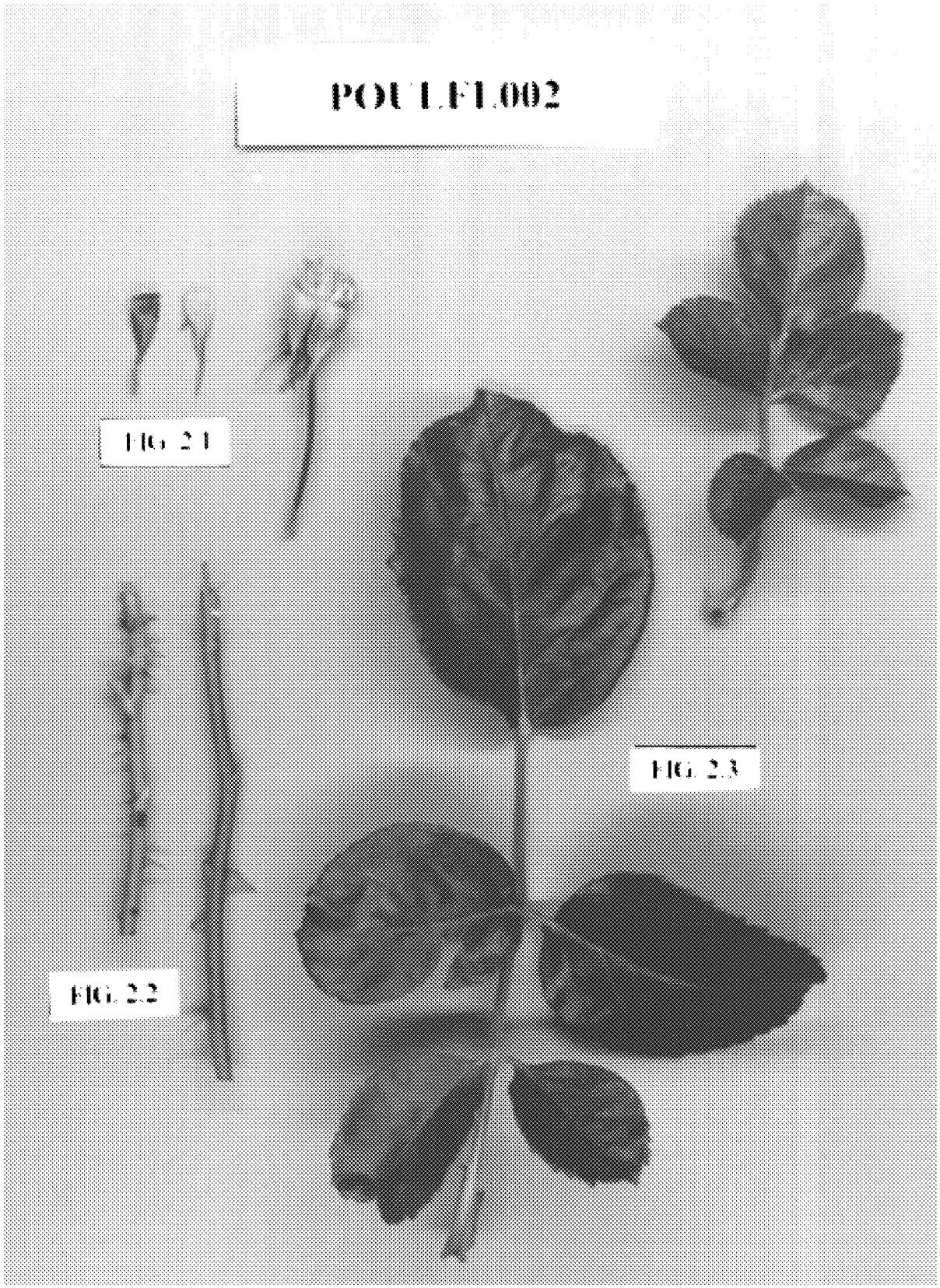
POULF1.002
FIG. 2.1
FIG. 2.2
FIG. 2.3